United States Patent
Sulatycke

(10) Patent No.: US 10,019,818 B2
(45) Date of Patent: Jul. 10, 2018

(54) CONCURRENT FORWARD- AND BACK-PROJECTION ITERATIVE RECONSTRUCTION SYSTEM

(71) Applicant: Toshiba Medical Systems Corporation, Otawara-shi (JP)

(72) Inventor: Peter D. Sulatycke, Arlington Heights, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/645,460

(22) Filed: Mar. 12, 2015

(65) Prior Publication Data

US 2016/0267688 A1    Sep. 15, 2016

(51) Int. Cl.
    *G06T 11/00* (2006.01)
    *A61B 5/055* (2006.01)

(52) U.S. Cl.
    CPC .......... *G06T 11/006* (2013.01); *G06T 11/008* (2013.01); *A61B 5/055* (2013.01); *G06T 2207/10072* (2013.01); *G06T 2207/30004* (2013.01); *G06T 2211/424* (2013.01)

(58) Field of Classification Search
    CPC ............. G06T 11/006; G06T 2211/424; G06T 11/008; G06T 2211/421; G06T 11/003; G06T 2207/20224
    See application file for complete search history.

(56) References Cited

U.S. PATENT DOCUMENTS

| | | | |
|---|---|---|---|
| 2013/0101192 A1* | 4/2013 | Nakanishi | G06T 11/006 382/131 |
| 2015/0055847 A1* | 2/2015 | Jeong | G06T 11/006 382/131 |
| 2016/0210741 A1* | 7/2016 | Brendel | G06T 11/006 |

* cited by examiner

Primary Examiner — Kenny Cese
(74) Attorney, Agent, or Firm — Oblon, McClelland, Maier & Neustadt, L.L.P.

(57) ABSTRACT

A method, a non-transitory computer-readable storage medium, and an image processing apparatus are provided for performing iterative reconstruction to generate a medical image. The method includes generating, by circuitry of the image processing apparatus, a first image data set by separately back projecting subsets of a first view data set. Each of the subsets of the first view data set corresponds to one of a plurality of different non-overlapping sections of the medical image to be reconstructed. The method further includes generating, by the circuitry, a second view data set by separately forward projecting subsets of the first image data set. Each of the subsets of the first image data set corresponds to one of the sections of the medical image to be reconstructed. Further, the step of generating the second view data set starts before the step of generating the first image data set is completed.

17 Claims, 10 Drawing Sheets

```
/* pseudo code - does not consider view sets */
collected_views        /* original views collected by CT system */
view_data = 0          /* initial calculated views */
image_data = standard_back_projection (collected_views)  /* initial image volume data set
created */

For i = 1 to I Volumes  /* image volume iterations */

For j = 1 to J+1 Tiles  /* volume, is broken into J tiles */ load tile_data_j if ((i != I) and (j != J+1)) { /* not last volume iteration and not last tile iteration */

For k = 1 to K Views   /* Forward Projection */
                                If Tile_j projection lands on View_k
                                        Load bounding box of view_data_k for Tile_j projection on View_k
                                                FP tile_data_j onto View_k to update view_data_k
                                                save updated view_data_k
                                        Endif Tile
                        Endfor Views
                        /* tile_data_j has contributed to all views at this point */
                } endif if (j != 1) {
                        For k = 1 to K Views         /* Backward Projection */
                                If Tile_j projection lands on View_k
                                        Load bounding box of collected_views_k for Tile_j projection
on View_k
                                        Load bounding box of view_data_k for Tile_j projection on
View_k
                                        diff_view_data = collected_views_k - view_data_k
                                        BP diff_view_data and update tile_data_{j-1}
                                Endif Tile_j
                        Endfor Views
                        save tile_data_{j-1}  /* tile_data_{j-1} is complete at this point */
                }

Endfor Tiles
        /* all tiles have been BP and FP at this point, as a result an updated image data set has
been created */

Endfor Volumes
```

FIG. 5

CONCURRENT FORWARD- AND BACK-PROJECTION ITERATIVE RECONSTRUCTION SYSTEM

FIELD

Embodiments disclosed herein generally relate to iterative reconstruction, involving forward- and back-projections, performed for medical imaging (e.g., computed tomography (CT), positron emission tomography (PET), magnetic resonance imaging (MRI), and X-ray).

BACKGROUND

Radiographic imaging, in its simplest expression, is an X-ray beam traversing an object and a detector relating the overall attenuation per ray. From this conceptual definition, several steps are required to properly construct an image. Several elements affect how the actual image reconstruction is performed.

In computed tomography, the operation that transforms an N-dimension image into an N-dimension set of line integrals is called a forward-projection. One example of this operation is the physical process that generates an X-ray image of an object. After logarithmic conversion, an X-ray image is well approximated as the line integral projection of the distribution of the object's linear attenuation coefficient. The transpose operation is called back-projection. This technique is used in filtered back-projection and in iterative reconstruction, which are used in conventional reconstruction algorithms.

The methods for forward- and back-projection in X-ray and CT systems can be generally classified as ray-driven methods or pixel-driven methods. A critical drawback associated with these methods is that they introduce artifacts in the constructed image. A distance-driven method addresses the above issues. However, the distance-driven method of forward- and back-projections incurs a significant number of processing operations (i.e., weighting and multiplication operations) that tend to increase the image reconstruction time.

Further, an iterative reconstruction system typically performs back-projection on all views within a set of views before any forward-projection occurs. In other words, a data partition size in the iterative reconstruction system includes the whole volume. Specifically, N views are back projected to create a volume of pixels. The volume is then looped over and forward projected to create a new set of N views. This processing requires a large amount of bandwidth to move the volumes in and out of the system. In addition, since the data partition is the size of the volume, there is very little opportunity to parallelize the forward- and back-projection processing. Thus, the performance of the iterative reconstruction system is constrained.

Accordingly, methods for improving the overall image reconstruction time and bandwidth usage in back- and forward-projection processes are needed.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein:

FIG. 5 depicts pseudo-code for performing concurrent back- and forward-projections according to one embodiment of the present disclosure;

DETAILED DESCRIPTION

Figure 1:
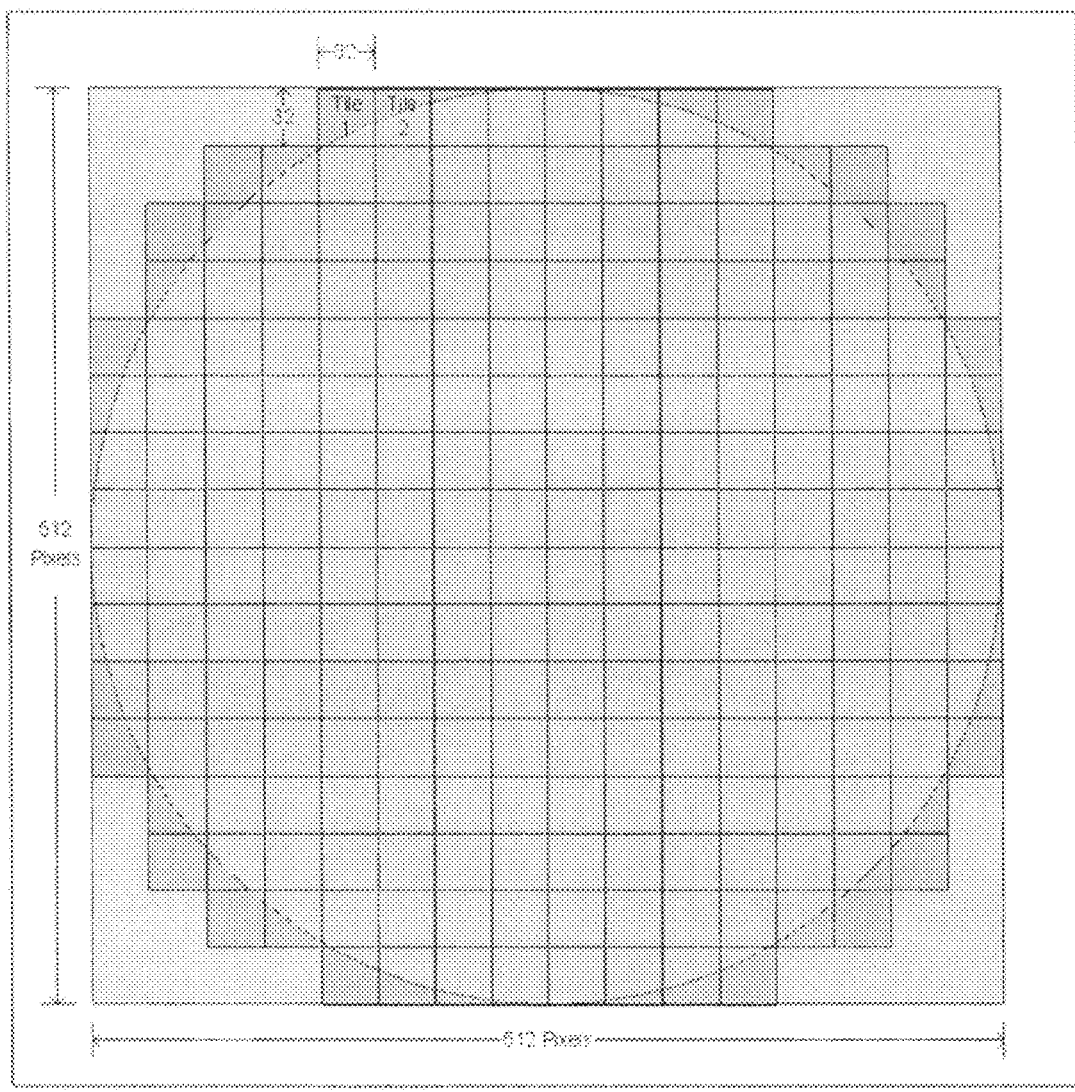
FIG. 1 depicts an exemplary image broken into a plurality of sections or tiles.

While the present disclosure is susceptible of embodiment in many different forms, there is shown in the drawings and will herein be described in detail specific embodiments, with the understanding that the present disclosure of such embodiments is to be considered as an example of the principles and not intended to limit the present disclosure to the specific embodiments shown and described. In the description below, like reference numerals are used to describe the same, similar or corresponding parts in the several views of the drawings.

In one embodiment, there is provided an image processing apparatus. The image processing apparatus includes circuitry that is configured to generate a first image data set by separately back projecting subsets of a first view data set. Each of the subsets of the first view data set corresponds to one of a plurality of different non-overlapping sections of a medical image to be reconstructed. Further, the subsets of the first view data set for different non-overlapping sections of the medical image may overlap. The circuitry is further configured to generate a second view data set by separately forward projecting subsets of the first image data set. Each of the subsets of the first image data set corresponds to one of the sections of the medical image to be reconstructed. The circuitry starts the generation of the second view data set before the generation of the first image data set is completed.

In another embodiment, there is provided a method for performing iterative reconstruction to generate a medical image. The method includes generating, by circuitry of an image processing apparatus, a first image data set by separately back projecting subsets of a first view data set. Each of the subsets of the first view data set corresponds to one of a plurality of different non-overlapping sections of the medical image to be reconstructed. The method further includes generating, by the circuitry, a second view data set by separately forward projecting subsets of the first image data set. Each of the subsets of the first image data set corresponds to one of the sections of the medical image to be reconstructed. Further, the step of generating the second view data set starts before the step of generating the first image data set is completed.

In another embodiment, there is provided a non-transitory computer-readable storage medium storing instructions which when executed by a computer causes the computer to perform the method for performing iterative reconstruction to generate the medical image, as described above. The present disclosure relates to improving overall image reconstruction time and bandwidth usage in back- and forward-projection processes. In order to perform iterative reconstruction with a data partition size consisting of a whole volume of pixels (or a whole image), a large amount of bandwidth is required to move the volume pixel data set into and out of the iterative reconstruction system. This bandwidth requirement can severely constrain the performance of the system. One option to implement such a system is to perform back-projection and forward-projection in separate processors with a high-bandwidth link between the processors. However, this implementation does not allow forward- and back-projections to be performed at the same time. Another option to implement such a system is to perform forward-projection and back-projection one at a time in a single processor. The second option is impractical in a FPGA (field-programmable gate array) and requires high bandwidth in a GPGPU (general-purpose graphics processing unit). Further, iterative reconstruction systems having a data partition size consisting of the whole volume of pixels do not scale well when additional processors are incorporated into those systems.

Embodiments described herein use a smaller data partition size by breaking a volume of pixels (or image) to be reconstructed into a plurality of sections (e.g., pixel tiles). FIG. 1 illustrates an example of a two-dimensional image that is broken into a plurality of different sections. Each of the sections is processed one at a time, which allows both back-projection and forward-projection to be performed at the same time in an iterative reconstruction system. As a result, volume data of the volume of pixels does not need to be moved into and out of the system as often. This can significantly reduce the bandwidth requirements of the volume data, which is three-dimensional and very large compared to a view data set. Only a subset of the view data set is loaded to create a full volume. Thus, the bandwidth required to move the volume data is much larger than the view data set. Embodiments described herein reduce the number of times the volume data set needs to be moved to/from memory. This results in a large savings over a full iterative method. Since the majority of the bandwidth requirement comes from volume data, overall bandwidth can be significantly decreased and performance increased.

Although FIG. 1 illustrates a two-dimensional image is broken into a plurality of sections (e.g., 32×32 pixels per tile), embodiments of the present disclosure are also applicable to images of other dimensions or sizes, e.g., three-dimensional images. In the case of three-dimensional images, the image may be broken into three-dimensional sections.

Figure 2:
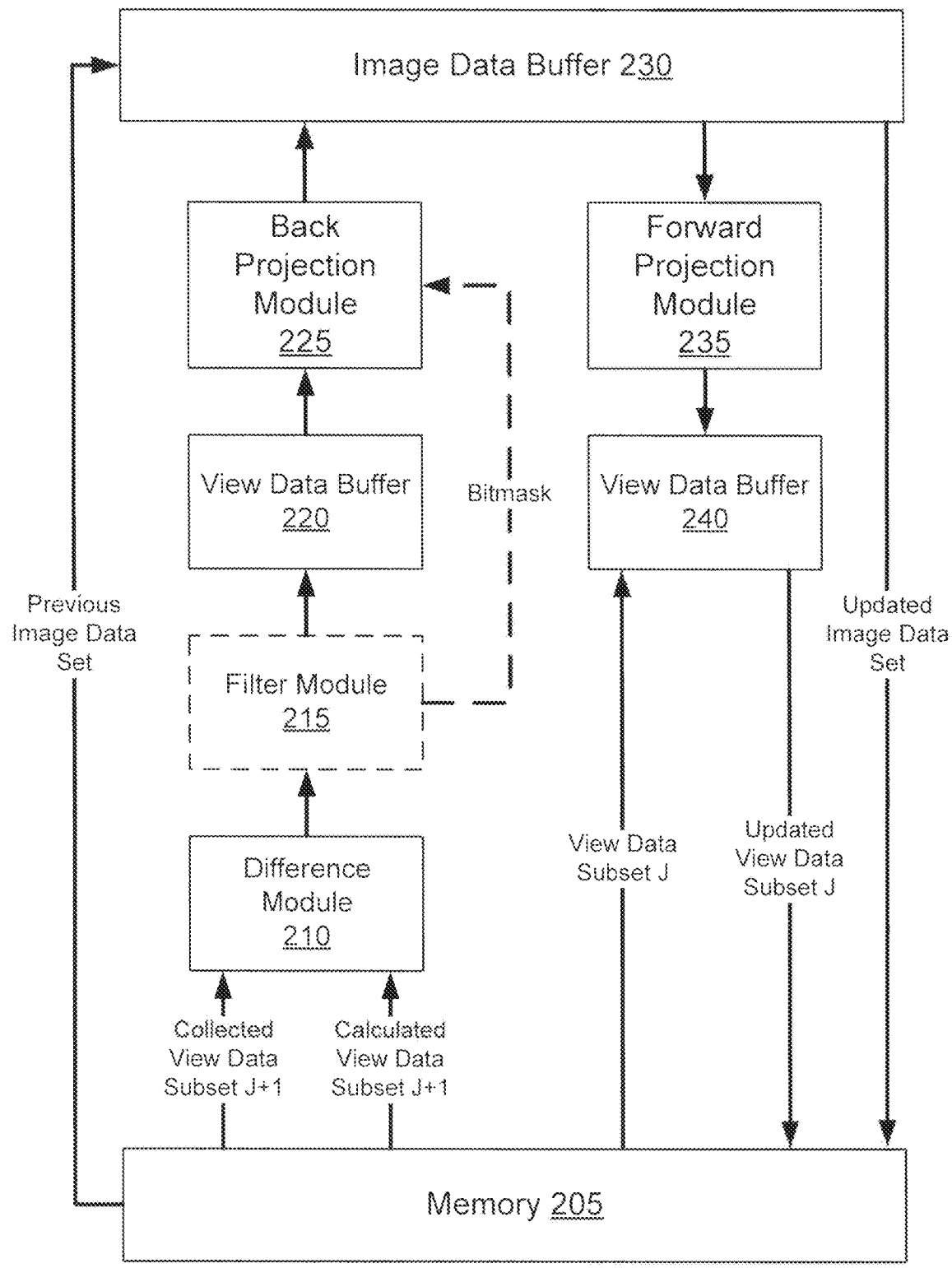
FIG. 2 depicts concurrent back- and forward-projections, on a section basis, according to one embodiment of the present disclosure.

FIG. 2 shows an overview of a process of the iterative reconstruction system for performing concurrent forward- and back-projections according to one embodiment. An initial image data set is created by back projecting all collected view data for each of the sections of the image to be reconstructed. The collected view data set is generated by and received from a medical imaging device. A back-projection module 225 performs the back-projections based on the collected view data set stored in a memory 205. In other embodiments, the initial image data set is created without breaking the initial image into a plurality of sections, is set to a predetermined image, and/or is received from an external source.

Figure 3:
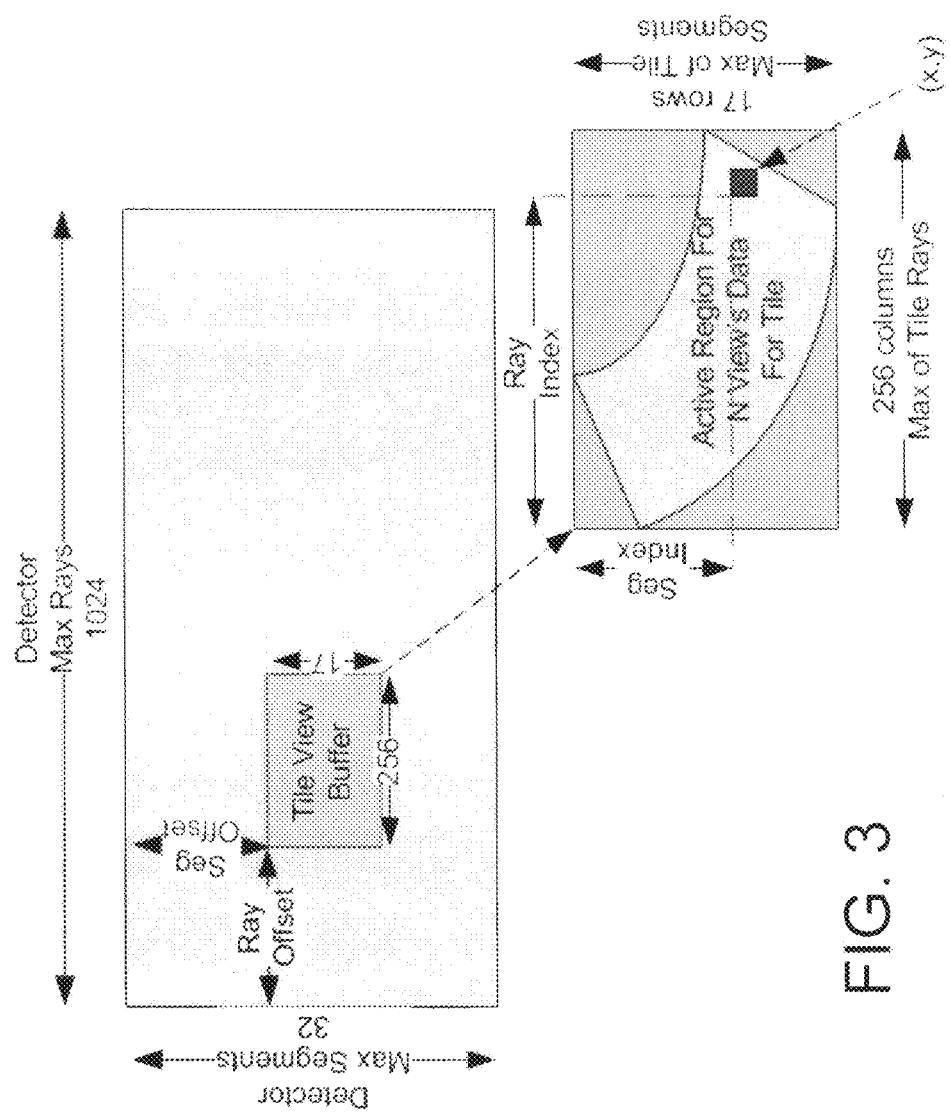
FIG. 3 depicts an example of view buffer data needed to support forward- and back-projection for one section.

To generate the initial image data set, and subsequent image data sets, the iterative reconstruction system determines which view data subset corresponds to the respective section of the image. FIG. 3 illustrates one embodiment for making this determination. Specifically, FIG. 3 illustrates an example of a view data subset for one view that corresponds to one image section projected onto a detector plane. An extent around the projection of the image section is used to determine exactly which subset of view data is affected or needed during processing. The active region illustrated in FIG. 3, in one embodiment, approximates the curvature of the detector. Further, FIG. 3 illustrates exemplary numbers of detector segments and detector rays.

Depending on the embodiment, the view data subset corresponding to the image section includes view data from one or a plurality of different views. The different views correspond to, for example, different projection angles. For example, the medical imaging device includes at least one detector that surrounds an object to be imaged. The medical imaging device collects view data based on measurements of at least one of emission and transmission radiation from the object by the detector at the different projection angles, each of the projection angles corresponding to a different field of view.

The image data output by the back-projection module 225 is written to an image data buffer(s) 230. The resulting image data set for the plurality of sections are then sent to a forward-projection module 235 to create a calculated view data set, which in certain embodiments includes a view data subset for each of one or more views (e.g., for each of 15 views). In one embodiment, forward-projections are separately performed to create a calculated view data subset for each of the one or more views. Since image data for more than one section contributes to the same view data, partial view data is read into view data buffer 240 and accumulated with previously created view data. This process is concurrently repeated until all sections have been processed and a first iteration of calculated view data has been created. Thus, at least a subset of the calculated view data is generated concurrently with the generation of a subset of the initial image data set.

Back-projection now begins to generate a first iteration of image data, where the collected view data and first iteration of calculated view set data are read in and subtracted by the difference module 210, provided to and buffered by the view data buffer 220, and back projected by the back-projection module 225. The back-projection results for the sections are accumulated into the image data in the image data buffer(s) 230. Further, the initial image data set, which corresponds to the previous image data set, is read in so that new results can be added in. Subsequently, an updated image data set is written out to the memory 205 from the image data buffer(s) 230 after each back-projection iteration. This process is then repeated until all view data have been updated via forward- and back-projections. At this point, post processing of the image data, such as a gradient-descent algorithm, with line search can be performed.

Post-processing may be performed in a post-processing module (e.g., implemented by circuitry such as a CPU) or the forward-projection module 235 may be temporally replaced by a post-processing module. For example, FPGAs allow partial reconfiguration that would enable this capability. In one embodiment, the iterative reconstruction system allows post processing to occur concurrently with the back-projection of image sections. For example, post processing can be performed on one or more of the image sections while back-projection is performed on another one or more of the image sections.

As further described below, the forward- and back-projections are then repeated for another iteration. This continues for a predetermined number of iterations or until a predetermined noise threshold is determined to be reached, for example using filter module 215.

In certain embodiments, an additional optimization is implemented in the back-projection module 225. If the subtracted view data subset calculated in the difference module 210 is small enough, there is no need to back project the subtracted view data subset. An optional filter logic unit 215 can be used to test the difference view data (i.e., subtracted view data) and store validity results in a bitmask. The bitmask is then used in the back-projection module 225 to determine if back-projection should be done with the subtracted view data subset.

Further, in certain embodiments, bandwidth requirements of the iterative reconstruction system are further reduced by processing multiple adjacent image sections at the same time. Since there is an overlap of view data needed for adjacent image sections, some view data can be loaded once for multiple image sections. In one embodiment, this is accomplished by incorporating a global cache that passes needed data to individual local caches working on separate sections.

Although various techniques (e.g., pixel or ray-driven projection techniques) can be used for forward- and back-projection, it is beneficial in certain embodiments that the projection technique be reversible so that it converges more easily. In addition, it is beneficial in certain embodiments if the projection techniques have similar data access and computation requirements. Thus, certain embodiments of the present disclosure utilize the distance-driven algorithm, which is algorithmically simple and does not require significant computation resources.

As described above, embodiments of the present disclosure provide a reduction in the bandwidth requirement for loading and reading volumes (or image data). In certain embodiments, the bandwidth is significantly reduced because forward-projection can occur with partial volume data section results instead of having to temporarily write volume data to memory and then read it back to complete processing. The bandwidth saving can become quite significant since this process is repeated extensively in iterative reconstruction algorithms. Embodiments of the present disclosure have well-balanced bandwidth requirements for forward- and back-projections, making their implementation simple. Another main advantage of the present disclosure is that is scales well with multiple pipelines within a FPGA and with multiple FPGAs or other types of circuitry (e.g., multi-core processors, etc.).

Figure 4A:
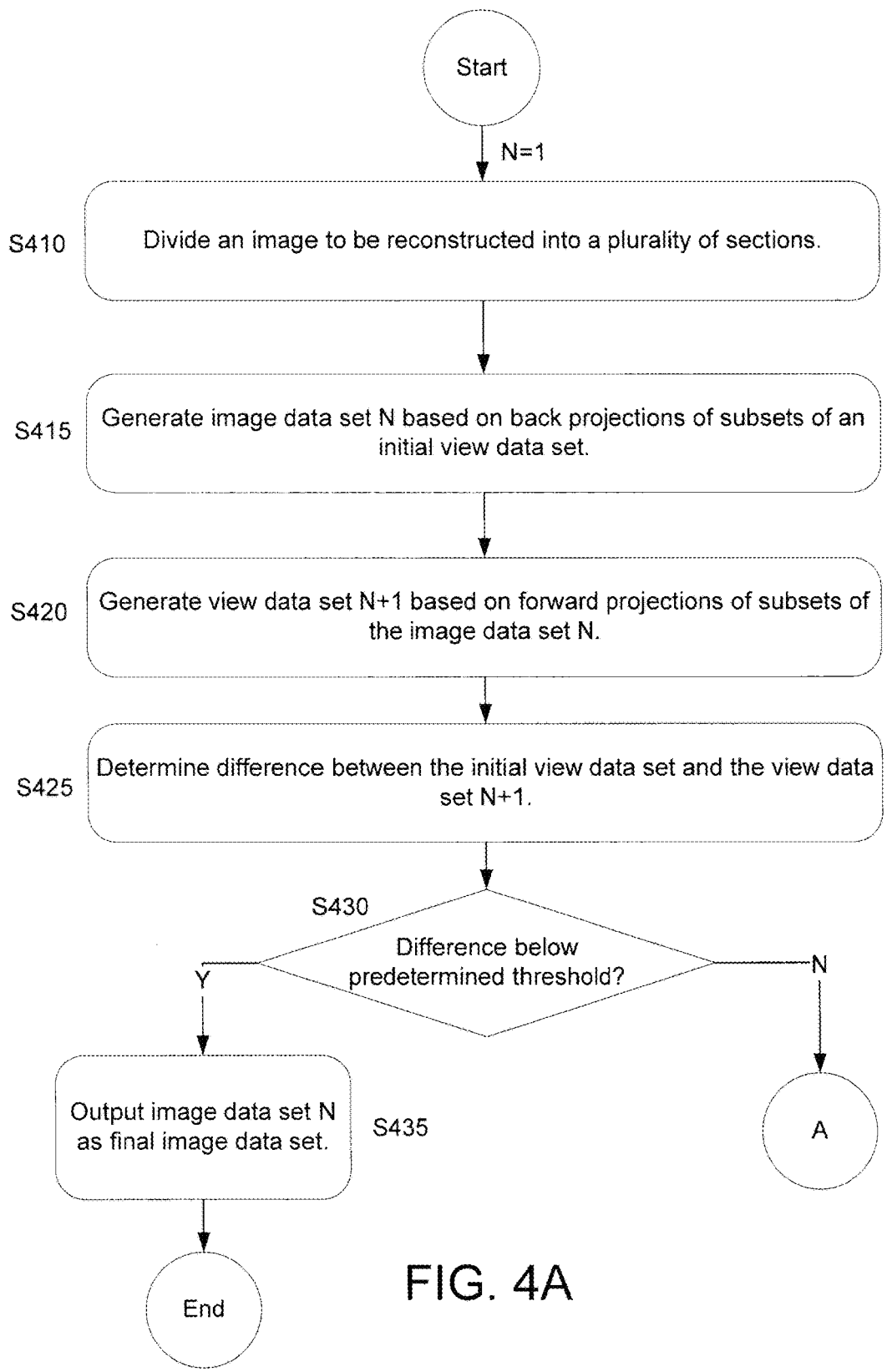
FIGS. 4A and 4B are flowcharts illustrating the steps of performing concurrent back- and forward-projections according to one embodiment of the present disclosure.
Figure 4B:
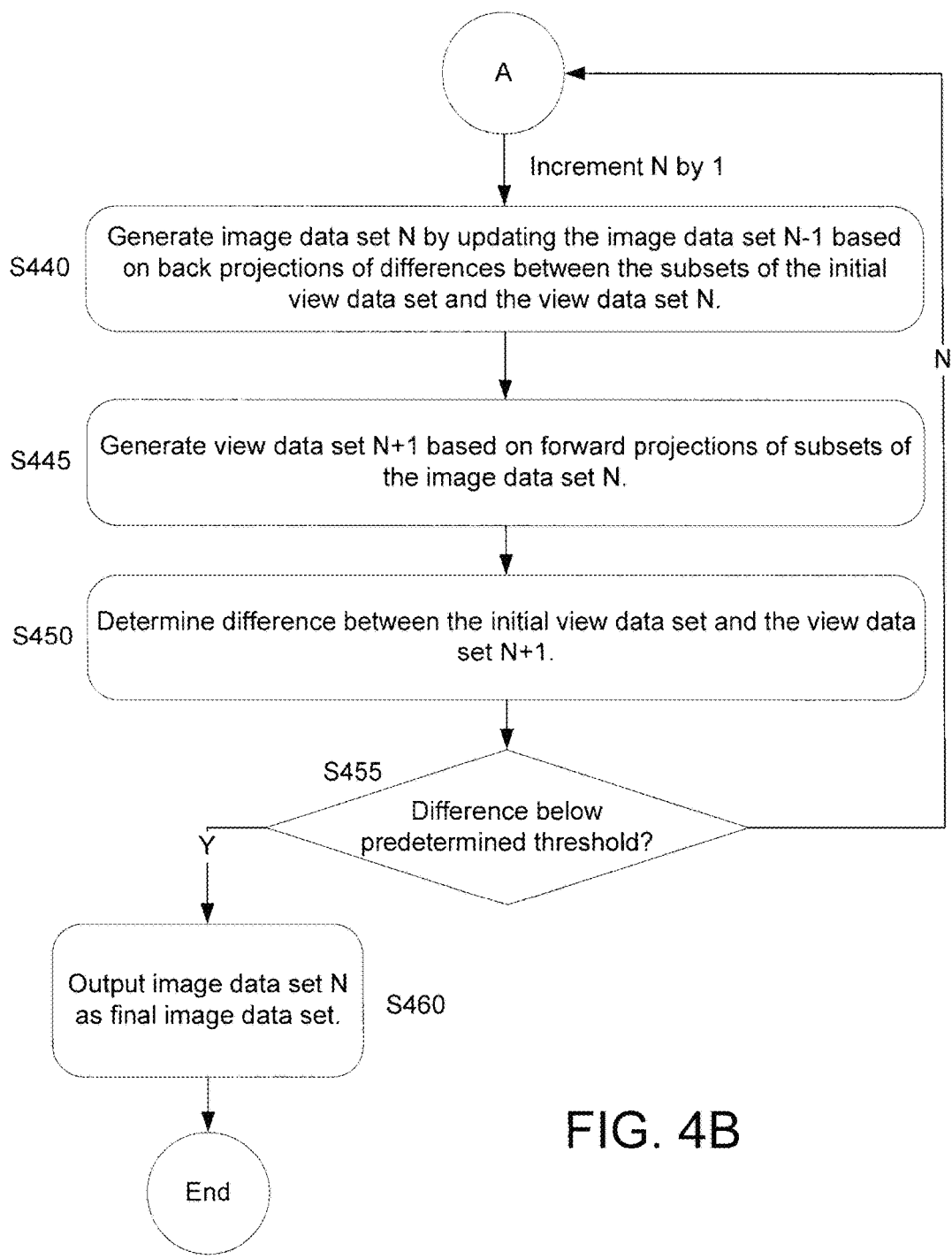

FIGS. 4A and 4B depict flow diagrams of an exemplary iterative image reconstruction process that is performed by an iterative reconstruction system, which includes an image processing apparatus, according to one embodiment.

As illustrated in FIG. 4A, the reconstruction process begins at step S410, at which time an image to be generated is divided into a plurality of sections for subsequent processing. In one embodiment, the image to be generated is divided into a plurality of different non-overlapping sections. Further, in certain embodiments, the number of sections is input or selected by a user of the iterative reconstruction system. In other embodiments, the number of sections is a predetermined value that is fixed by the iterative reconstruction system.

In step S415, the iterative reconstruction system generates an image data set N based on separate back-projections of subsets of an initial view data set. The initial view data set is a set of view data that is collected by a medical imaging device, such as a CT scanner or other types of medical imaging devices used for MRI, PET, and single positron emission computed tomography (SPECT). Each of the subsets of the initial view data set corresponds to a different section of the image to be reconstructed. Each of the subsets of the initial view data set may contain view data for one or a plurality of different views. The different views are of an object measured by the medical imaging device, for example, at different projection angles or views.

To generate the image data set N, the iterative image reconstruction system identifies which subsets of the collected view data set contribute to each of the sections of the image to be reconstructed. The identification of subsets may be performed in the manner illustrated in FIG. 3. For each of the sections, the collected view data that contributes to the respective section is identified and then back projected. Depending on the embodiment, the back-projections performed on the identified subsets of the collected view data are part of a single view or a plurality of different views.

In step S420, a view data set N+1 (e.g., a first iteration of calculated view data) is generated based on separate forward-projections of subsets of the image data set N. In one embodiment, subsets of the view data set N+1 for the image sections is generated sequentially. First, for each view, a determination is made as to whether the image section projection lands on the respective view. If the image section projection is determined to land on the respective view, a bounding box of new view data for the image section projection on the respective view is loaded. Subsequently, a subset of the image data set N corresponding to the image section is forward projected to update the new view data.

In step S425, the iterative reconstruction system determines the difference between the initial view data set and the view data set N+1. The differences are determined per image section and/or based on one or more views. Corresponding subsets of the initial view data and the view data N+1 of each of the image sections are identified and separately subjected to the difference comparison.

In step S430, an optional determination is made as to whether the difference(s) identified in step S425 is below a predetermined threshold. The threshold comparison can be performed on an image section and/or view basis or based on a combination, or all, of the image sections and/or views. If the difference is determined to be below the predetermined threshold, the first iteration of the image data set N is output as a final image data set in step S435. For example, the iterative reconstruction system generates the final image based on the image data set N and outputs the final image for display to a user of the iterative reconstruction system. However, if the difference is greater than or equal to the predetermined threshold, or the optional determination step S430 is not performed, the reconstruction process advances to step S440 in FIG. 4B, at which time the next iteration of image data and calculated view data are generated.

In step S440, the iterative reconstruction system generates the next iteration of image data for each of the image sections based on one or more back-projections of a previous iteration of calculated view data. For example, for each image section, the iterative reconstruction system separately back projects the difference between corresponding subsets of collected and calculated view data of the respective image section. The respective image section is then updated based on the result of the back-projection. For example, in the case of the expectation maximization (EM) algorithm, the back-projection produces a correction factor that is multiplied by a previous iteration of an image section estimate and divided by a weighting term that controls the strength of the image correction factor.

Steps S440, S445, S450, S455, and S460 are similar to steps S415, S420, S425, S430, and 435 respectively, but differ in that steps S415, S420, S425, S430, and S435 apply to the first iteration of the reconstruction process while steps S440, S445, S450, S455, and S460 apply to subsequent iterations.

In certain embodiments, the iterative reconstruction system is configured to terminate the reconstruction process when a predetermined number of iterations have been reached. For example, after step S440, the iterative reconstruction system determines whether the predetermined number of iterations has been reached and, if determined to be reached, terminates the reconstruction process and outputs the image data set N generated at step S440 as a final image data set.

FIG. 5 depicts pseudo code for an iterative reconstruction process according to one embodiment of the present disclosure. The iterative reconstruction process includes the generation of a plurality of volume iterations, similar to the process illustrated in FIGS. 4A-4B. The pseudo code demonstrates that forward and back-projection can be performed concurrently by having each projection process work on different subsets of the image data set at the same time.

The circuitry of the iterative reconstruction system disclosed herein is easily scalable beyond, for example, one FPGA, processor, or GPGPU. Each sub-circuitry (e.g., FPGA) will work on different subsets of a view data set (e.g., corresponding to different views) while the view data subsets are updated and transmitted between sub-circuitry (e.g., FPGAs). There is no need to send image data between the sub-circuitry. During forward-projection, view data from each particular view will only be updated by at most one sub-circuitry at a time. This avoids spending time transmitting and combining view results together.

Figure 6:
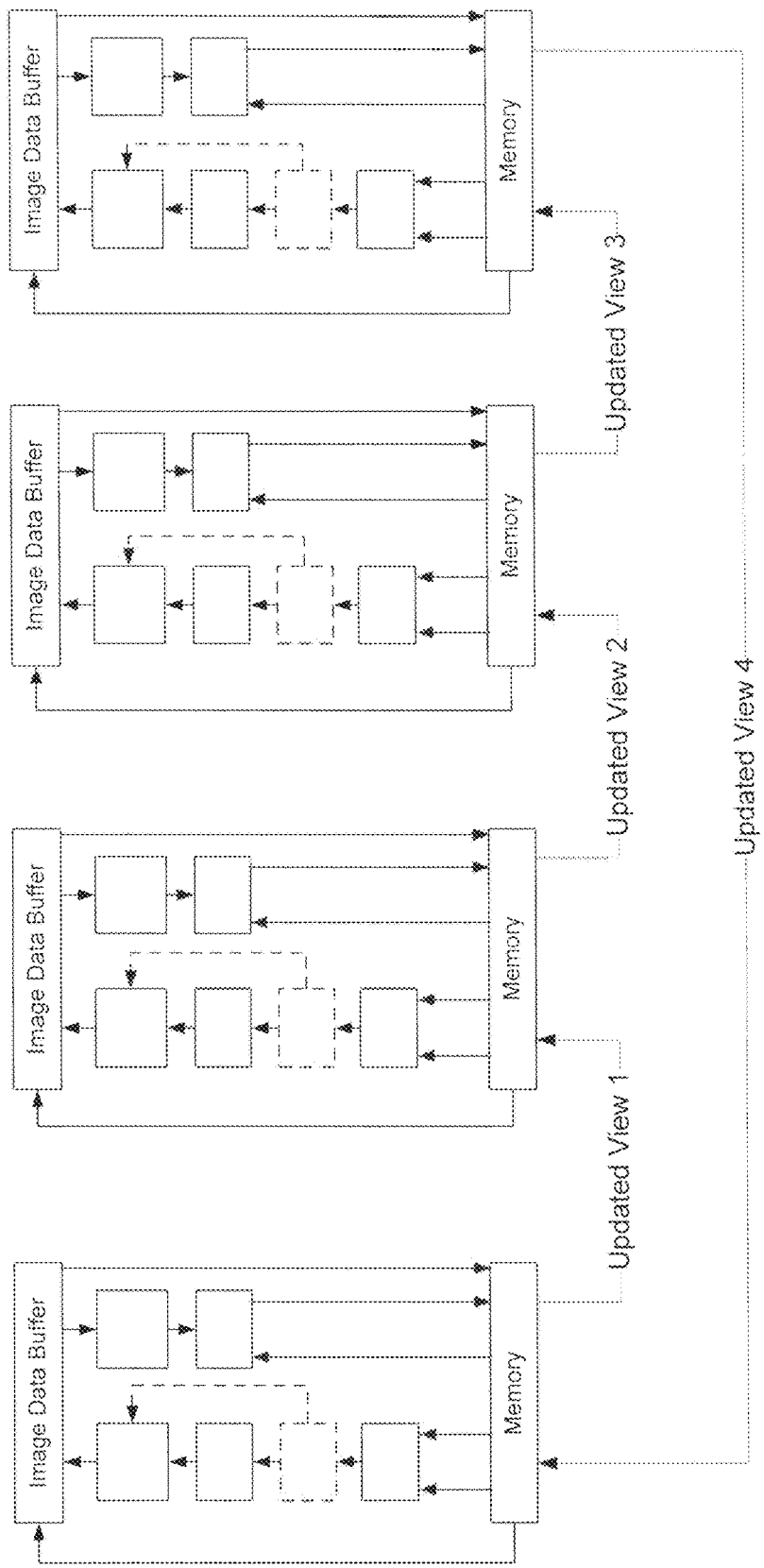
FIG. 6 depicts an example of multiple iterative reconstruction systems working on the same image.

FIG. 6 shows an example of a four FPGA system that processes four views in a view data set. Initial processing starts with each FPGA (or sub-circuitry) creating view data for a different view. The updated view data is then sent to a neighboring FPGA so that they can be further updated. This process then repeats for subsequent views. Once all views are processed, the resulting views are distributed to all FPGAs so that they can be used in the next back-projection iteration. In one embodiment, the transmission time of the final views can be hidden by back projecting different views in the FPGAs at the same time. Updated views can then be sent from one FPGA to the next FPGA during subsequent projections. This system easily scales to the number of views in a view set, for example 15. This could be increased to 30 or even higher if results from more than one FPGA are combined before being further processed, although this would require more transmission of view data and time to perform the accumulation step.

Figure 7:
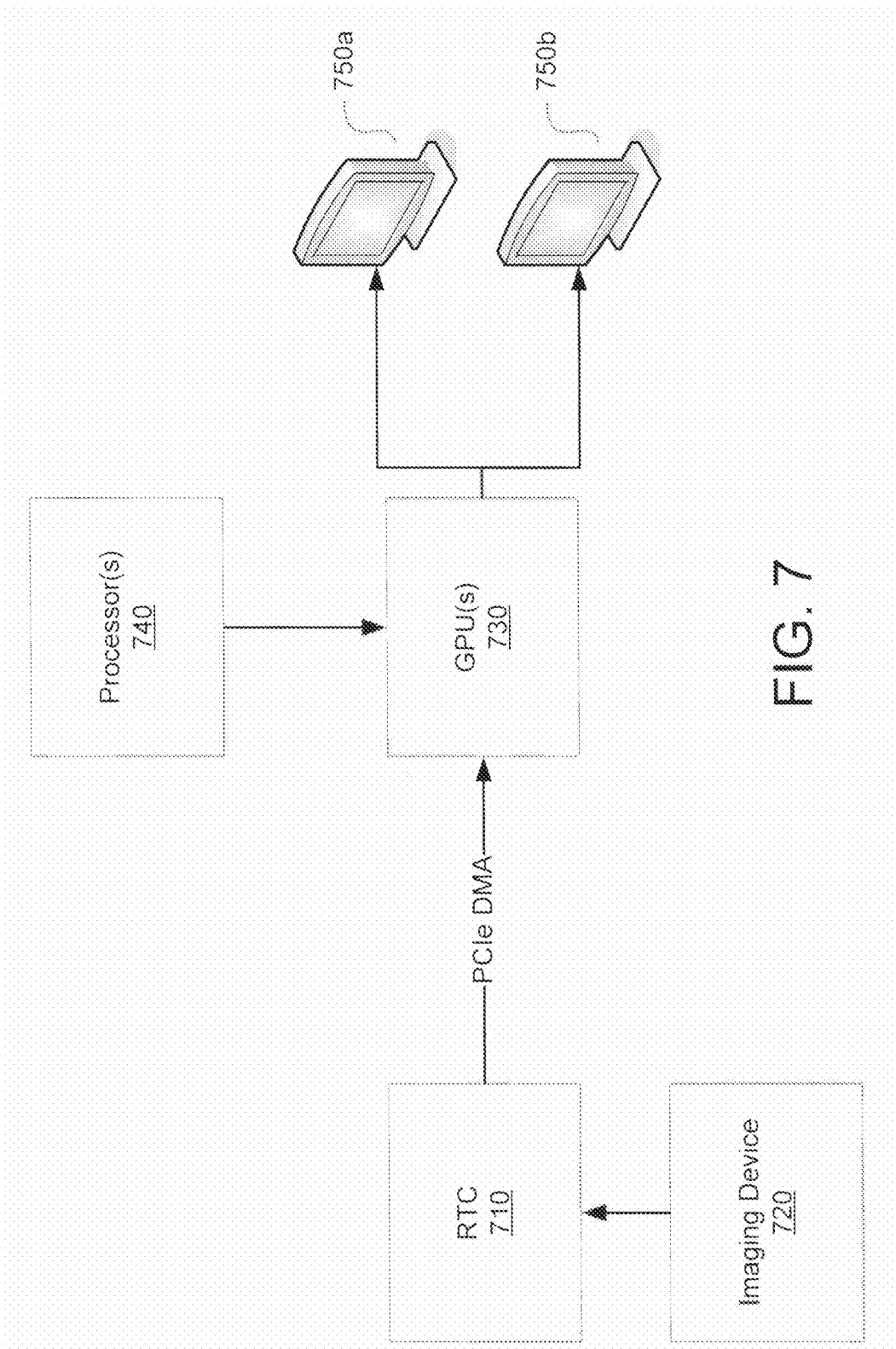
FIG. 7 illustrates exemplary components of an iterative reconstruction system according to one embodiment of the present disclosure.

The iterative reconstruction system described herein can be implemented using circuitry embodied, for example, in a computer processing apparatus or programmable logic. FIG. 7 illustrates data movement between components of an iterative reconstruction system according to one embodiment. A real-time controller (RTC) 710 receives a view data set (e.g., collected view data) from a medical imaging device 720 (e.g., a CT scanner) and provides the view data set to the one or more GPUs 730 for processing. In certain embodiments the RTC 710 is an FPGA-based PCIe board that is configured to handle real-time data movement and control, including to/from the one or more GPUs 730. The RTC 710 provides the view data set via direct memory access to the one or more GPUs 730. The RTC 710 may also provide kernel processing parameters to the one or more GPUs 730 along with the view data set.

One or more processors 740 is coupled to the one or more GPUs 730 and is configured to provide GPU commands such as run one or more kernels, copy data, and display results. The one or more GPUs 730 process one or more images and outputs the display results (e.g., a reconstructed medical image generated based on a final image data set) on one or more displays 750a, 750b.

Figure 8:
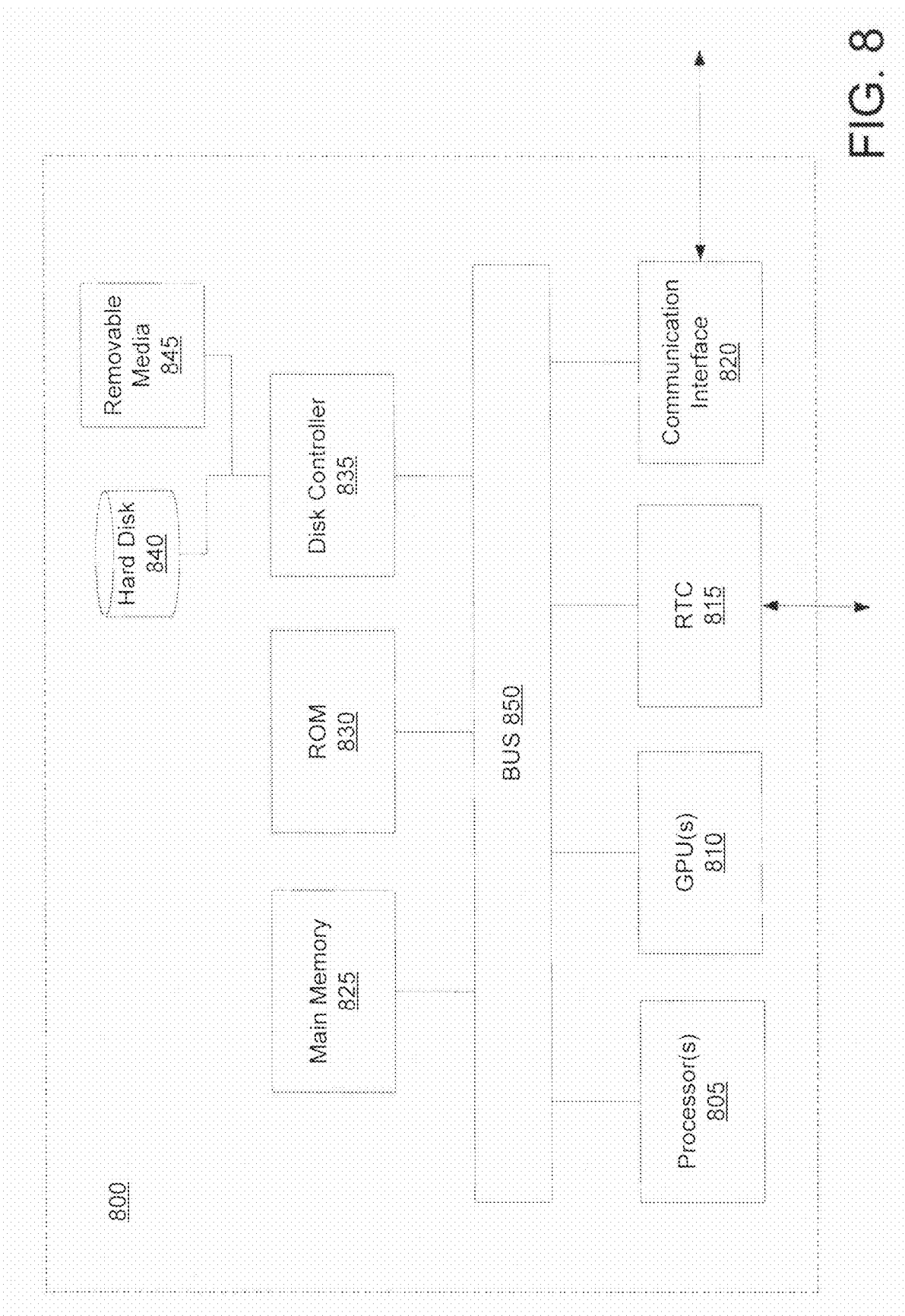
FIG. 8 illustrates a computer system that may be used to control a medical imaging device and upon which embodiments of the present disclosure may be implemented.

FIG. 8 illustrates an exemplary computer system 800 incorporating circuitry that performs iterative reconstruction to reconstruct one or more images. The computer system is an aggregate of a plurality of component elements (e.g., apparatuses, modules (parts), etc.). All the component elements may or may not be housed in a single enclosure. Therefore, a plurality of apparatuses each housed in a separate enclosure and connected via a network, or other connections, are considered a system, and a single apparatus formed by a plurality of modules housed in a single enclosure are also regarded as a system.

The computer system 800 includes processor(s) 805, GPU(s) 810, RTC 815, a communication interface 820, a main memory 825, a read only memory (ROM) 830, and a disk controller 835, which are connected to each other via one or more buses 850.

Depending on the embodiment, one or a combination of the processor(s) 805 and GPU(s) 810 is configured to perform the iterative reconstruction of the image, as discussed above. For example, different cores or processors of the processor(s) 805 are utilized to perform concurrent back- and forward-projections. In another example, different pipelines or GPUs of the GPU(s) 810 are utilized to perform the concurrent back- and forward-projections.

The processor(s) 805 and GPU(s) 810 can be configured to carry out multiple operations or computations tasks in a parallel manner. In one embodiment, one processor core, processor, GPU, or GPU pipeline implements the back-projection module 225 and another processor core, processor, GPU, or GPU pipeline implements the forward-projection module 240. Further, the difference module 210, filter module 215, view data buffer 220 and view data buffer 240 may implemented by circuitry of the same or a different processor or GPU.

Further, the disk controller 835 is coupled to the bus 850 to control one or more storage devices for storing information and instructions, such as a hard disk 840, and a removable media drive 845 (e.g., floppy disk drive, read-only compact disc drive, read/write compact disc drive, compact disc jukebox, tape drive, and removable magneto-optical drive). The storage devices may be added to the computer system 800 using an appropriate device interface (e.g., small computer system interface (SCSI), integrated device electronics (IDE), enhanced-IDE (E-IDE), direct memory access (DMA), or ultra-DMA). Such interfaces may also be utilized by any of the other components of the computer system 800.

The computer system 800 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The processor(s) 805 executes one or more sequences of one or more instructions contained in a memory, such as the main memory 825. Such instructions may be read into the main memory 825 from another computer readable medium, such as the hard disk 840 or the removable media drive 845. One or more processors in a multi-processing arrangement may also be employed to execute the sequences of instructions contained in main memory 825. In alternative embodiments, hard-wired circuitry may be used in place of or in combination with software instructions. Thus, embodiments are not limited to any specific combination of hardware circuitry and software.

As stated above, the computer system 800 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes. Stored on any one or on a combination of computer readable media, the present disclosure includes software for controlling the computer system 800, for driving a device or devices for implementing the embodiments of the present disclosure, and for enabling the computer system 800 to interact with a human user. Such software may include, but is not limited to, device drivers, operating systems, and applications software. Such computer readable media further includes the computer program product of the present disclosure for performing all or a portion (if processing is distributed) of the processing performed in implementing the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor(s) 805 for execution. A computer readable medium may take many forms, including but not limited to, non-volatile media or volatile media. Non-volatile media includes, for example, optical, magnetic disks, and magneto-optical disks, such as the hard disk 840 or the removable media drive 845. Volatile media includes dynamic memory, such as the main memory 825. Transmission media, on the contrary, includes coaxial cables, copper wire and fiber optics, including the wires that make up the bus 850. Transmission media also may also take the form of acoustic or light waves, such as those generated during radio wave and infrared data communications.

Various forms of computer readable media may be involved in carrying out one or more sequences of one or more instructions to processor(s) 805 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 800 may receive the data on the telephone line and place the data on the bus 850. The bus 850 carries the data to the main memory 825, from which the processor(s) 805 retrieves and executes the instructions. The instructions received by the main memory 825 may optionally be stored on storage device 840 or 845 either before or after execution by the processor(s) 805.

The communication interface 820 is coupled to the bus 850. The communication interface 820 provides a two-way data communication coupling to a network link that is connected to, for example, a local area network (LAN), or to another communications network such as the Internet. For example, the communication interface 820 may be a network interface card to attach to any packet switched LAN. As another example, the communication interface 820 may be an integrated services digital network (ISDN) card. Wireless links may also be implemented. In any such implementation, the communication interface 820 sends and receives electrical, electromagnetic or optical signals that carry digital data streams representing various types of information.

The network link typically provides data communication through one or more networks to other data devices. For example, the network link may provide a connection to another computer through a local network (e.g., a LAN) or through equipment operated by a service provider, which provides communication services through a communications network. The local network and the communications network use, for example, electrical, electromagnetic, or optical signals that carry digital data streams, and the associated physical layer (e.g., CAT 6 cable, coaxial cable, optical fiber, etc.). The signals through the various networks and the signals on the network link and through the communication interface 820, which carry the digital data to and from the computer system 800 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as un-modulated baseband data through a "wired" communication channel and/or sent within a predetermined frequency band, different than baseband, by modulating a carrier wave. The computer system 800 can transmit and receive data, including program code, through the network(s), the network link and the communication interface 820.

Figure 9:
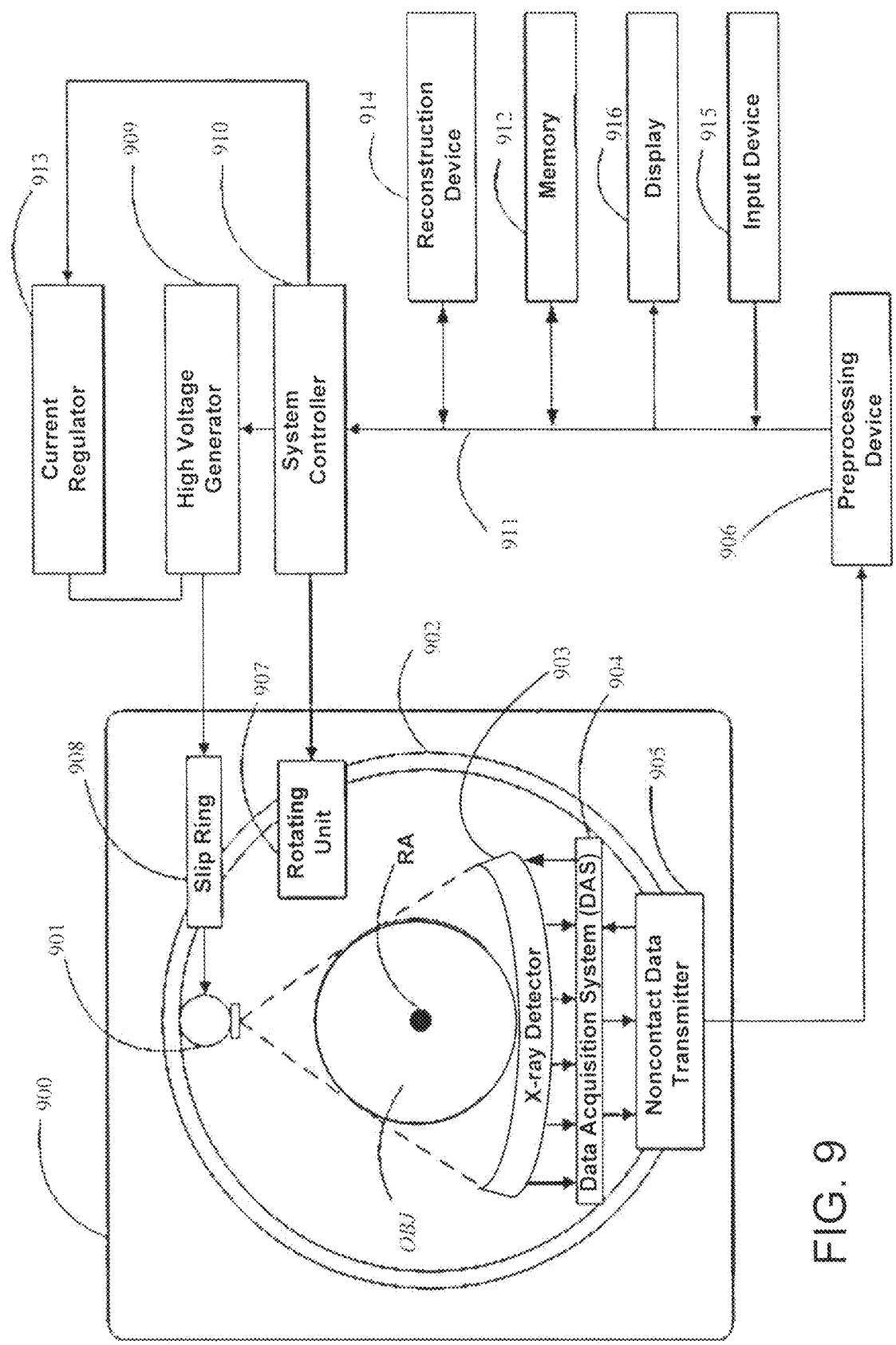
FIG. 9 illustrates a schematic of an exemplary computed tomography scanner.

FIG. 9 illustrates an exemplary radiography gantry included in a CT apparatus or scanner. As shown in FIG. 9, a radiography gantry 900 is illustrated from a side view and further includes an X-ray tube 901, an annular frame 902, and a multi-row or two-dimensional-array-type X-ray detector 903. The X-ray tube 901 and X-ray detector 903 are diametrically mounted across an object OBJ on the annular frame 902, which is rotatably supported around a rotation axis RA. A rotating unit 907 rotates the annular frame 902 at a high speed, such as 0.4 sec/rotation, while the object OBJ is being moved along the axis RA into or out of the illustrated page.

An embodiment of an X-ray computed tomography apparatus according to the present disclosure will be described below with reference to the views of the accompanying drawing. Note that X-ray computed tomography apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present disclosure can be applied to either type. In this case, the rotate/rotate type, which is currently the mainstream, will be exemplified.

The multi-slice X-ray CT apparatus further includes a high voltage generator 909 that generates a tube voltage applied to the X-ray tube 901 through a slip ring 908 so that the X-ray tube 901 generates X-rays. The X-rays are emitted towards the object OBJ, whose cross sectional area is represented by a circle. The X-ray detector 903 is located at an opposite side from the X-ray tube 901 across the object OBJ for detecting the emitted X-rays that have transmitted through the object OBJ. The X-ray detector 903 further includes individual detector elements or units.

The CT apparatus further includes other devices for processing the detected signals from X-ray detector 903. A data acquisition circuit or a Data Acquisition System (DAS) 904 converts a signal output from the X-ray detector 903 for each channel into a voltage signal, amplifies the signal, and further converts the signal into a digital signal. The X-ray detector 903 and the DAS 904 are configured to handle a predetermined total number of projections per rotation (TPPR). Examples of TPPRs include, but are not limited to 900 TPPR, 900-1800 TPPR, and 900-3600 TPPR.

The above-described data is sent to a preprocessing device 906, which is housed in a console outside the radiography gantry 900 through a non-contact data transmitter 905. The preprocessing device 906 performs certain corrections, such as sensitivity correction on the raw data. A memory 912 stores the resultant data, which is also called projection data at a stage immediately before reconstruction processing. The memory 912 is connected to a system controller 910 through a data/control bus 911, together with a reconstruction device 914, input device 915, and display 916. The system controller 910 controls a current regulator 913 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 901 and the X-ray detector 903 are diametrically mounted on the annular frame 902 and are rotated around the object OBJ as the annular frame 902 is rotated about the rotation axis RA. In the fourth-generation geometry system, the detectors are fixedly placed around the patient and an X-ray tube rotates around the patient. In an alternative embodiment, the radiography gantry 900 has multiple detectors arranged on the annular frame 902, which is supported by a C-arm and a stand.

The memory 912 can store the measurement value representative of the irradiance of the X-rays at the X-ray detector unit 903. Further, the memory 912 can store a dedicated program for executing the iterative image reconstruction methods described herein.

The reconstruction device 914 can execute the iterative image reconstruction methods discussed herein. Further, the reconstruction device 914 can execute pre-reconstruction processing image processing such as volume rendering processing and image difference processing as needed.

The pre-reconstruction processing of the projection data performed by the preprocessing device 906 can include correcting for detector calibrations, detector nonlinearities, polar effects, noise balancing, and material decomposition.

Post-reconstruction processing performed by the reconstruction device 914 can include filtering and smoothing the image, volume rendering processing, and image difference processing as needed. The reconstruction device 914 can use the memory 916 to store, e.g., projection data, reconstructed images, calibration data and parameters, and computer programs.

The reconstruction device 914 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 912 can be non-volatile, such as ROM, EPROM, EEPROM or FLASH memory. The memory 912 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 914 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions, for example as illustrated in FIG. 6.

In one implementation, the reconstructed images can be displayed on a display 916. The display 916 can be an LCD display, CRT display, plasma display, OLED, LED or any other display known in the art.

The memory 912 can be a hard disk drive, CD-ROM drive, DVD drive, FLASH drive, RAM, ROM or any other electronic storage known in the art.

While some of the embodiments described above are directed to CT scanning systems, the present disclosure is not limited thereto, but can be applied to other modalities, including, e.g., CT, MRI, PET, X-ray, and SPECT, and combinations thereof.

While certain embodiments have been described, these embodiments have been presented by way of example only, and are not intended to limit the scope of the present disclosure. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the present disclosure.

The invention claimed is:

1. An image processing apparatus, comprising:
 circuitry configured to
  separately back project subsets of a first view data set to generate subsets of a first image data set, each of the subsets of the first image data set including first image data corresponding to one of a plurality of non-overlapping sections of a medical image to be reconstructed, and each of the subsets of the first view data set corresponding to one of the plurality of different non-overlapping sections of the medical image to be reconstructed, and
  separately forward project the subsets of the first image data set to generate subsets of a second view data set, wherein
 the circuitry is configured to start the generation of the second view data set based on a part of the subsets of the first image data set for which the generation has been completed and before the generation of all of the subsets of the first image data set is completed such that the back projection of part of the subsets of the first view data set is performed concurrently with the forward projection of part of the subsets of the first image data set.

2. The image processing apparatus according to claim 1, wherein the circuitry is further configured to:
 generate subsets of a second image data set by updating the first image data set according to back-projections of differences between subsets of a collected view data set and the subsets of the second view data set, each of the subsets of the collected view data set and each of the subsets of the second view data set corresponding to one of the sections of the medical image to be reconstructed, the collected view data set being collected by a medical imaging device,
 generate the reconstructed medical image based on the second image data set, and
 output the reconstructed medical image for display.

3. The image processing apparatus according to claim 2, wherein the circuitry is further configured to
 perform post-processing on the subsets of the second image data set, each of the subsets of the second image data set corresponding to one of the sections of the medical image to be reconstructed, and
 generate the reconstructed medical image based on the post processed second image data set.

4. The image processing apparatus according to claim 3, wherein the circuitry is further configured to start the post processing of a part of the subsets of the second image data set, for which the generation has been completed, before the generation of all of the subsets of the second image data set is completed.

5. The image processing apparatus according to claim 2, wherein the circuitry is further configured to start the generation of the second image data set after the generation of the second view data set is completed.

6. The image processing apparatus according to claim 1, wherein the circuitry is further configured to generate the first image data set by updating a previously generated image data set according to back-projections of differences between subsets of a collected view data set and the subsets of the first view data set, the collected view data set being collected by a medical imaging device.

7. The image processing apparatus according to claim 1, wherein the circuitry is further configured to forward project one of the subsets of the first image data set corresponding to a first one of the sections while one of the subsets of the first view data set corresponding to a second one of the sections is back projected.

8. The image processing apparatus according to claim 1, wherein
 the circuitry includes first sub-circuitry and second sub-circuitry;
 the first sub-circuitry is configured to
  generate the first image data set for a first view by back projecting the subsets of the first view data set corresponding to the first view, and
  generate the second view data set for the first view by forward projecting the subsets of the first image data set for the first view; and
 the second sub-circuitry is configured to
  generate the first image data set for a second view by back projecting the subsets of the first view data set corresponding to the second view; and
  generate the second view data set for the second view by forward projecting the subsets of the first image data set for the second view.

9. A method for performing iterative reconstruction to generate a medical image, the method comprising:
 separately back projecting, by circuitry of an image processing apparatus, subsets of a first view data set to generate subsets of a first image data set, each of the subsets of the first image data set including first image data corresponding to one of a plurality of non-overlapping sections of the medical image to be reconstructed, and each of the subsets of the first view data set corresponding to one of the plurality of different non-overlapping sections of the medical image to be reconstructed; and
 separately forward projecting, by the circuitry, subsets of the first image data set to generate subsets of a second view data set, wherein
 the generation of the second view data set starts based on a part of the subsets of the first image data set for which generation has been completed and before the generation of all of the subsets of the first image data set is completed such that the back projection of part of the subsets of the first view data set is performed concurrently with the forward projection of part of the subsets of the first image data set.

10. The method according to claim 9, further comprising:
 generating, by the circuitry, subsets of a second image data set by updating the first image data set according to back-projections of differences between subsets of a collected view data set and the subsets of the second view data set, each of the subsets of the collected view data set and each of the subsets of the second view data set corresponding to one of the sections of the medical image to be reconstructed, the collected view data set being collected by a medical imaging device;
 generating the reconstructed medical image based on the second image data set; and
 outputting the reconstructed medical image for display.

11. The method according to claim 10, further comprising:
 performing post-processing on the subsets of the second image data set, each of the subsets of the second image data set corresponding to one of the sections of the medical image to be reconstructed, wherein
 the step of generating the reconstructed medical image includes generating the reconstructed medical image based on the post processed second image data set.

12. The method according to claim 11, wherein the step of performing post processing of a part of the subsets of the second image data set, for which the generation has been completed, starts before the step of generating the second image data set is completed.

13. The method according to claim 10, wherein the step of generating the second image data set starts after the step of generating the second view data set is completed.

14. The method according to claim 9, wherein the step of generating the first image data set comprises:
generating the first image data set by updating a previously generated image data set according to back-projections of differences between subsets of a collected view data set and the subsets of the first view data set, the collected view data set being collected by a medical imaging device.

15. The method according to claim 9, wherein the step of generating the second view data set comprises:
forward projecting one of the subsets of the first image data set corresponding to a first one of the sections while one of the subsets of the first view data set corresponding to a second one of the sections is back projected in the step of generating the first image data set.

16. The method according to claim 9, wherein
the step of generating the first image data set includes
generating, by first sub-circuitry of the circuitry, the first image data set for a first view by back projecting the subsets of the first view data set corresponding to the first view,
generating, by second sub-circuitry of the circuitry, the first image data set for a second view by back projecting the subsets of the first view data set corresponding to the second view; and
the step of generating the second view data set includes
generating, by the first sub-circuitry of the circuitry, the second view data set for the first view by forward projecting the subsets of the first image data set for the first view, and
generating, by the second sub-circuitry of the circuitry, the second view data set for the second view by forward projecting the subsets of the first image data set for the second view.

17. A non-transitory computer-readable storage medium storing instructions which when executed by a computer causes the computer to perform method for performing iterative reconstruction to generate a medical image, the method comprising:
separately back projecting subsets of a first view data set to generate subsets of a first image data set, each of the subsets of the first image data set including first image data corresponding to one of a plurality of non-overlapping sections of the medical image to be reconstructed, and each of the subsets of the first view data set corresponding to one of the plurality of different non-overlapping sections of the medical image to be reconstructed; and
separately forward projecting subsets of the first image data set to generate subsets of a second view data set, wherein
the generation of the second view data set starts based on a part of the subsets of the first image data set for which generation has been completed and before the generation of all of the subsets of the first image data set is completed such that the back projection of part of the subsets of the first view data set is performed concurrently with the forward projection of part of the subsets of the first image data set.

* * * * *